US007914814B2

(12) United States Patent
Fossel

(10) Patent No.: US 7,914,814 B2
(45) Date of Patent: *Mar. 29, 2011

(54) TOPICAL DELIVERY OF ARGININE OF CAUSE BENEFICIAL EFFECTS

(75) Inventor: Eric T. Fossel, Grand Isle, VT (US)

(73) Assignee: Strategic Science & Technologies, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/932,227

(22) Filed: Sep. 17, 1997

(65) Prior Publication Data

US 2002/0041903 A1  Apr. 11, 2002

(51) Int. Cl.
*A61K 31/198* (2006.01)
(52) U.S. Cl. .......................... 424/450; 514/565
(58) Field of Classification Search .................. 514/310, 514/478, 479, 565; 424/718, 450
See application file for complete search history.

(56) References Cited

U.S. PATENT DOCUMENTS

| | | | |
|---|---|---|---|
| 4,681,897 A * | 7/1987 | Brand ............................ 514/557 |
| 4,702,913 A | 10/1987 | Marty |
| 4,732,892 A | 3/1988 | Sarpotdar et al. |
| 4,871,839 A * | 10/1989 | Gibson ........................ 536/55.1 |
| 4,950,654 A | 8/1990 | Horn |
| 4,976,952 A | 12/1990 | Lang et al. |
| 5,028,435 A | 7/1991 | Katz et al. |
| 5,180,743 A | 1/1993 | Watanabe et al. |
| 5,210,099 A | 5/1993 | Mody et al. |
| 5,254,331 A | 10/1993 | Mausner |
| 5,332,758 A | 7/1994 | Nakata et al. |
| 5,391,550 A | 2/1995 | Carniglia et al. |
| 5,405,919 A * | 4/1995 | Keefer et al. .................. 525/377 |
| 5,428,070 A * | 6/1995 | Cooke et al. .................. 514/557 |
| 5,439,938 A | 8/1995 | Snyder et al. |
| 5,476,852 A | 12/1995 | Cauwenbergh |
| 5,498,420 A * | 3/1996 | Mentrup Edgar et al. .... 424/450 |
| 5,505,958 A | 4/1996 | Bello et al. |
| 5,527,797 A | 6/1996 | Eisenberg et al. |
| 5,538,740 A | 7/1996 | Abad |
| 5,543,430 A * | 8/1996 | Kaesemeyer .................. 514/565 |
| 5,576,351 A | 11/1996 | Yoshimura et al. |
| 5,595,753 A * | 1/1997 | Hechtman .................... 424/436 |
| 5,629,002 A * | 5/1997 | Weuffen et al. ............... 424/401 |
| 5,632,981 A * | 5/1997 | Saavedra et al. ........... 424/78.08 |
| 5,648,101 A | 7/1997 | Tawashi |
| 5,691,423 A | 11/1997 | Smith et al. |
| 5,698,738 A * | 12/1997 | Garfield et al. ................ 564/112 |
| 5,714,472 A * | 2/1998 | Gray et al. ....................... 514/21 |
| 5,762,963 A | 6/1998 | Byas-Smith |
| 5,789,442 A | 8/1998 | Garfield et al. |
| 5,807,957 A | 9/1998 | Samour et al. |
| 5,853,768 A * | 12/1998 | Altadonna .................... 424/667 |
| 5,891,459 A | 4/1999 | Cooke et al. .................. 424/439 |
| 5,891,472 A | 4/1999 | Russell |
| 5,895,658 A | 4/1999 | Fossel |
| 5,906,822 A | 5/1999 | Samour et al. |
| 5,911,980 A | 6/1999 | Samour et al. |
| 5,922,332 A | 7/1999 | Fossel |
| 5,925,372 A * | 7/1999 | Berner et al. ................. 424/448 |
| 5,939,094 A | 8/1999 | Durif |
| 5,976,566 A | 11/1999 | Samour et al. |
| 6,036,977 A | 3/2000 | Drizen |
| 6,103,275 A | 8/2000 | Seitz et al. |
| 6,117,872 A | 9/2000 | Maxwell et al. |
| 6,207,713 B1 * | 3/2001 | Fossel ............................ 514/565 |
| 6,242,229 B1 | 6/2001 | Pineau et al. |
| 6,287,601 B1 | 9/2001 | Russell |
| 6,375,672 B1 | 4/2002 | Aksan et al. |
| 6,387,081 B1 | 5/2002 | Cooper |
| 6,444,234 B1 | 9/2002 | Kirby et al. |
| 6,448,267 B1 | 9/2002 | Anggard et al. |
| 6,451,337 B1 | 9/2002 | Smith et al. |
| 6,458,841 B2 | 10/2002 | Fossel |

(Continued)

FOREIGN PATENT DOCUMENTS

CA        2337772        1/2000

(Continued)

OTHER PUBLICATIONS

Cooper et al. The Transdermal Delivery of Drugs, vol. II p. 57-62, 1986.*
Birder, CAPLUS AN 1998:548084, 1998.*
Hirvonen et al., "Effect of diffusion potential . . . ",Journal of Controlled Release, 56, (1998),p. 33-39.*
International Search Report for International Application Serial No. PCT/US05/05726 dated Sep. 9, 2005.
International Search Report for International Application Serial No. PCT/US05/13228 dated Jul. 5, 2005.

(Continued)

*Primary Examiner* — Jeffrey C Mullis
(74) *Attorney, Agent, or Firm* — Wolf, Greenfield & Sacks, P.C.

(57) ABSTRACT

A preparation is disclosed for producing enhanced blood flow in tissue thus causing beneficial effects such as promoting hair growth on scalp tissue lacking sufficient hair, restoring normal sexual function in males with erectile dysfunction. Specifically, this is a preparation which provides local delivery of the amino acid L-arginine, an important biological precursor to the main substance which is responsible for relaxation of blood vessels permitting enhancement of blood flow. In the preferred embodiments, the L-arginine is provided so that it can be topically applied to the scalp or penis. The preparation also contains an agent which aids in the transfer of L-arginine into the tissue. In the preferred embodiments this agent overcomes the resistance to transfer caused by the high charge density of L-arginine. In the preferred embodiments this means is high ionic strength created by addition of choline chloride, magnesium chloride and sodium chloride. This preparation when applied nightly to scalp tissue lacking sufficient hair for a period of time causes substantial growth of hair on the scalp. Further, when applied to the penis of a subject with erectile dysfunction causes restoration of normal sexual function.

26 Claims, No Drawings

U.S. PATENT DOCUMENTS

| | | | |
|---|---|---|---|
| 6,511,991 B2 | 1/2003 | Hrabie et al. | |
| 6,538,033 B2 | 3/2003 | Bing | |
| 6,558,695 B2 | 5/2003 | Luo et al. | |
| 6,562,370 B2 | 5/2003 | Luo et al. | |
| 6,565,879 B1 | 5/2003 | Luo et al. | |
| 6,582,724 B2 | 6/2003 | Hsu et al. | |
| 6,586,000 B2 | 7/2003 | Luo et al. | |
| 6,602,912 B2 | 8/2003 | Hsu et al. | |
| 6,617,337 B1 | 9/2003 | Wilcox | |
| 6,716,436 B1 | 4/2004 | Seguin | |
| 6,719,997 B2 | 4/2004 | Hsu et al. | |
| 6,747,063 B2 | 6/2004 | Adams et al. | |
| 6,787,152 B2 | 9/2004 | Kirby et al. | |
| 6,835,392 B2 | 12/2004 | Hsu et al. | |
| 6,858,232 B2 | 2/2005 | Verbiscar | |
| 7,241,456 B2 | 7/2007 | Vromen | |
| 7,267,829 B2 | 9/2007 | Kirby et al. | |
| 7,442,690 B2 | 10/2008 | Prejean et al. | |
| 7,629,384 B2 | 12/2009 | Fossel | |
| 2002/0015713 A1 | 2/2002 | Murdock et al. | |
| 2002/0037854 A1 | 3/2002 | Breton et al. | |
| 2002/0168325 A1 | 11/2002 | Lerner | |
| 2002/0168424 A1* | 11/2002 | Shahinpoor et al. | 424/718 |
| 2007/0105763 A1* | 5/2007 | Ghosh | 514/12 |
| 2007/0253911 A1 | 11/2007 | Tamarkin et al. | |

FOREIGN PATENT DOCUMENTS

| | | |
|---|---|---|
| DE | 101 28 910 A1 | 12/2002 |
| EP | 0338291 A1 | 10/1989 |
| EP | 0391342 A1 | 10/1990 |
| EP | 0 424 028 A2 | 4/1991 |
| EP | 1210933 A1 | 3/2003 |
| FR | 1 553 063 A | 11/1967 |
| FR | 5940 | 4/1968 |
| FR | 2602678 | 2/1988 |
| FR | 2 740 453 A1 | 4/1997 |
| FR | 2 810 540 A1 | 12/2001 |
| GB | 2094142 | 9/1982 |
| JP | 04-005231 | 9/1992 |
| JP | 6-247832 | 9/1994 |
| JP | 7-53336 | 2/1995 |
| JP | 9/241156 A | 9/1997 |
| WO | WO 88/06034 A1 | 8/1988 |
| WO | WO 92/08705 | 5/1992 |
| WO | WO 94/09750 A1 | 5/1994 |
| WO | WO 95/13060 | 5/1995 |
| WO | WO 95/15147 | 6/1995 |
| WO | WO 95/15147 A1 | 6/1995 |
| WO | WO 96/08966 A1 | 3/1996 |
| WO | WO9608966 A1 * | 3/1996 |
| WO | WO 96/14748 | 5/1996 |
| WO | WO 96/29988 A1 | 10/1996 |
| WO | WO 97/10830 A1 | 3/1997 |
| WO | WO 97/16983 | 5/1997 |
| WO | WO 97/39760 A1 | 10/1997 |
| WO | WO 99/13717 A1 | 3/1999 |
| WO | WO 00/40215 A1 | 7/2000 |
| WO | WO 00/54773 A1 | 9/2000 |
| WO | WO 00/69469 A1 | 11/2000 |
| WO | WO 01/45713 A1 | 6/2001 |
| WO | WO 2006/096360 A1 | 9/2006 |

OTHER PUBLICATIONS

International Search Report for International Application Serial No. PCT/US05/13230 dated Oct. 28, 2005.

Pauly et al, *Liposomes containing amino acids and peptides and proteins for skin care*, Chemical Abstracts (1998), vol. 113, No. 65069.

Argiolas, A., et al., "Nitric Oxide is a Central Mediator of Penile Erection," *Neuropharmacology*, vol. 11, pp. 1339-1344 (1994).

Bunker, C.D., "Alteration in scalp blood flow after the epicutaneous application of 3% minoxidil and 0.1% hexyl nicotinate in alopecia," *Correspondence*, pp. 669.

DeBoer, E.M., "Does Topical Minoxidil Increase Skin Blood Flow? A Laser Doppler Flowmetry Study," *Acta Derm Venereo*, vol. 68, pp. 271-274 (1988).

Dietz, N. M., "Is nitric oxide involved in cutaneous vasodilation during body heating in humans?", *J. Appl. Physiol.*, vol. 76, No. 5, pp. 2047-2053 (1994).

Garban, H., "Effect of aging on nitric oxide-mediated penile erection in rats," *Am. J. Physiol.*, vol. 268, pp. 467-475 (1995).

I-Sheng, T., "Evaluation of Vasulogenic Impotence Using Dynamic Penile Washout Test," *J. Formosan Med. Assoc.*, vol. 89, No. 11, pp. 992-996 (1990).

Kirkeby, H.J., "Role of the L-arginine/nitric oxide pathway in relaxation of isolated human penile cavernous tissue and circumflex veins," *Acta Physiol Scand*, vol. 149, pp. 385-392 (1993).

Klemp, P., "Subcutaneous Blood Flow in Early Male Patter Baldness," *J. Invest Dermatol*, vol. 92, pp. 725-726 (1989).

Laan, E., et al., "Assessment of female sexual arousal: Response specificity and construct validity," *Psychophysiology*, vol. 32, pp. 476-485 (1995).

Mathias, B. J. et al., "Topical Capsaicin for Chronic Neck Pain," *Am. J. Phys. Med. Rehabil.*, vol. 74, No. 1, pp. 39-44 (1995).

Moody, J.A., et al., "Effects of Long-Term Oral Administration of L-Arginine on the Rat Erectile Response," *American Urological Association, Inc.*, vol. 158, pp. 942-947 (1997).

Owen, J.A., et al., "Topical Nitroglycerin: A Potential Treatment for Impotence," *The Journal of Urology*, vol. 141, pp. 546-548 (1989).

Singh, S. et al., "Response to digital arteries to endothelium dependent and independent vasocilators in patients with Raynaud's phenomenon," *European Journal of Clinical Investigation*, vol. 25, pp. 182-185 (1995).

Sonntag, M., et al., "Role of nitric oxide in local blood flow control in the anaesthetized dog," *European Journal of physiology*, pp. 194-199 (1992).

Tseng, L.F., et al., "Increase of nitric oxide production by L-arginine potentiates i.c.v. administered β-endorphin-induced antinociception in the mouse," *European Jouranal of Pharmacology*, vol. 212, pp. 301-303 (1992).

Wang, R. et al., "Nitric Oxide Mediates Penile Erection in Cats," *The Journal of Urology*, vol. 151, pp. 234-237 (1994).

Whitmore, S.E., et al, "Acute Effect of Topical Minoxidil on Digital Blood Flow in Patients with Raynaud's Phenomenon," *The Journal of Rheumatology*, vol. 11, No. 1, pp. 50-54 (1995).

International Search Report for International Application Serial No. PCT/US98/19429, international filing date Sep. 17, 1998.

Riedel, Markus W., et al., "Different Mechanisms of L-Arginine Induced Dilation of Brain Arterioles in Normotensive and Hypertensive Rats", CA: 122 (11) 130053t (Abstract), (1995).

Nakaki, T. et al., "Beneficial Circulatory Effect of $_L$-Arginine," *Jpn. J. Pharmacol.* 66, 167-171 (1994).

The Merck Index, An Encyclopedia of Chemicals, Drugs, and Biologicals, Twelfth Edition, p. 817.

Fossel, E., "Improvement of Temperature and Flow in Feet of Subjects with Diabetes with Use of a Transdermal Preparation of L-Arginine," *Diabetes Care* (2004); vol. 27, No. 1; p. 284-5.

Haldiya, K. et al., "Dermal ulcers and hypertension in salt workers," *Curr Sci* (2004); vol. 87, No. 8, p. 1139-41.

Matuszak, D. et al., "Thermodynamic Driving Force for Molecular Diffusion—Lattice Density Functional Theory Predictions," *J Non-Equilib Thermodyn* (2006); vol. 31, No. 4, p. 355-84.

Suhonen, T. M. et al., "Epidermal cell culture model derived from rat keratinocytes with permeability characteristics comparable to human cadaver skin," *Eu J Pharm Sci* (2003), vol. 20, p. 107-13.

Thompson, Paul D. "Exercise & Sports Cardiology" McGraw-Hill (USA), 2001, p. 372.

BioSpace Press Release "TransDermal Ibuprofen Development Complete: NDA To Be Filed" Dec. 16, 2004, author unknown, (publication on the Internet, http://biospace.com/news_story.aspx?NewsEntityId=18470820).

International Search Report and Written Opinion for International Application No. PCT/US2009/003750 mailed May 19, 2010.

International Search Report and Written Opinion for International Application No. PCT/US2009/003749 mailed May 19, 2010.

* cited by examiner

TOPICAL DELIVERY OF ARGININE OF CAUSE BENEFICIAL EFFECTS

BACKGROUND

1. Field of the Invention

This invention relates to topical application of a cream, gel, or other vehicle which contains substances such as L-arginine which delivers these substances into tissue for the purpose of producing beneficial effects such as growth of hair on the scalp, healing of leg ulcers secondary to diabetes or confinement to bed and overcoming erectile dysfunction, as well as beneficial effects through restoration of natural mechanisms based on improvement of local blood supply.

2. Prior Art

Approaches to improving local blood flow have been many and consist of both systemic and topical approaches. Many beneficial effects could be obtained should improvement in local blood flow be achieved since impairment of local blood flow causes a variety of negative consequences.

It has been recognized that deficiencies in blood flow in the scalp occur in male pattern baldness. See G. Duplechain et al., J. Louisiana State Med Soc. 146, 7 (1994); P Klemp et al., J Invests Dermatol 95, 725 (1989); S Toshitani et al., J Dermatol 17, 240 (1990). Topical minoxidil has been used as an agent for hair growth in male pattern baldness with varying results. Though the suggestion has been made that minoxidil operates through increase in the blood supply to the scalp, many investigators have failed to show such an effect. See E de Boer et al., Acta Dermato-Venereoligica 68, 271 (1988); C Bunker et al., British J Derm 117, 668 (1987).

It has long been recognized that impaired blood flow to the penis is a major cause of erectile failure (impotence) in men. See A Moradian et al. Am J. Med 85, 748, (1988); T Hwang et al. J Formosan Med Assoc 89, 992 (1990). Further it has been recognized by using isolated tissue in vitro and in animal experiments that nitric oxide is an important mediator of relaxation of the vessels in penile cavernous tissue. See H Kirkeby et al. Acta Physiol Scand 149, 385 (1993). Topical nitroglycerine has been used in the treatment of impotence because of its ability to dilate vessels. The results were inconclusive and the treatment not well tolerated because of the cardiac response to nitroglycerine. See S Negelev J Urology 143, 586 (1990).

Accordingly, several objects and advantages of the instant invention are to induce the growth of hair on portions of human scalp which has insufficient hair by means of enhancement of the body's natural mechanisms. It is yet another object of the instant invention to induce healing of superficial ulcers of the limbs by means of enhancement of the body's natural mechanisms. It is still another object of the instant invention to overcome erectile failure restoring natural male sexual function by means of enhancement of the body's own natural mechanisms.

SUMMARY OF THE INVENTION

It was discovered that topical application of a nitric oxide precursor, L-arginine, in its various forms contained in a variety of topical preparations, either by themselves or with other agents to aid in penetration, such as a high ionic strength environment, neutralization of its charge in a complex or by other means, or included in a liposome or other biological carrier, when administered to the scalp causes hair growth, when administered to superficial ulcers causes healing and when administered to the penis enhances erectile function.

In one embodiment of the invention, a penetrating cream containing L-arginine at an effective concentration and a salt, such as sodium chloride, at a concentration sufficient to create a hostile biophysical environment for the L-arginine in the cream is applied to nightly to the scalp containing a deficit of hair induces hair growth within 3-4 months.

Further, in accordance with this invention, a penetrating cream containing L-arginine in a concentration sufficient to produce the desired effect along with sodium chloride or other salts at a concentration sufficient to produce a hostile biophysical environment when applied to the penis induces firm and natural erections within 20 minutes.

Consequently, with the discovery of the present invention, a means to restore hair growth on a portion of scalp scarce in hair has been found. Further, with the discovery of the present invention, a means to heal superficial ulcers has been found. Additionally, with the discovery of the present invention, a means to overcome erectile dysfunction has been found.

In preferred embodiments, the delivery vehicle is a penetrating cream, the L-arginine is present as L-arginine hydrochloride (0.25 to 25%) in a concentration sufficient to produce the desired effect and the agent which creates the hostile biophysical environment is sodium chloride (0.25 to 25%) at a concentration sufficient to aid in tissue absorption.

These and other objects and features of the present invention will become apparent to those skilled in the art from reading the description of the invention, which follows.

DETAILED DESCRIPTION OF THE INVENTION

Nitric oxide causes increased local blood flow, which enables the growth of hair, which when applied to leg ulcers cause healing through use of the body's own mechanisms and when applied to a penis subject to erectile dysfunction causes restoration of normal sexual function. This effect is achieved by providing the biochemical substrate at the local site from which the controlling substance, nitric oxide is produced. Nitric oxide causes increases in local blood flow allowing the body's own healing cells and substances to reach the ulcer site. A method for increasing the local blood flow in tissue of a mammal involves topically administering to the mammal an effective amount of a nitric oxide precursor. The nitric oxide precursor is administered in a delivery vehicle wherein the delivery vehicle is a penetrating cream, a liquid, a lotion, an ointment or other topical preparation and wherein the nitric oxide precursor is L-arginine a salt, a complex or a derivative thereof.

One embodiment consists of a base cream with the properties of excellent absorption into the skin which also contains L-arginine hydrochloride (12.5% w/v), choline chloride (101/o), sodium chloride (5% w/v) and magnesium chloride (5% w/v). The components of the base cream may be those commonly found in hand creams, such as water, mineral oil, glyceryl stereate, squalene, propylene glycol stearate, wheat germ oil, glyceryl stearate, isopropyl myristate, steryl stearate, polysorbate 60, propylene glycol, oleic acid, tocopherol acetate, collagen, sorbitan stearate, vitamin A & D, triethanolamine, methylparaben, aloe vera extract, imidazolidinyl urea, propylparaben, and BHA.

In another embodiment the cream can comprise water (20-80%), mineral oil (3-18%) glyceryl stearate SE (0.5-12%) squalene (0.2-12%), cetyl alcohol (0.1-11%), propylene glycol stearate SE (0.1-I I %) wheat germ oil (0.1-6%) glyceryl stereate (0.16%) isopropyl myristate (0.1-6%) stearyl stearate (0.1-6%), polysorbate 60 (0.1-5%), propylene glycol (0 05-5%) tocopherol acetate (0.05-5%), collagen (0.05-5%), sorbitan stearate (0.05-5%), vitamin A&D (0.02-4%) triethanolamine (0.01-4%), methylparaben (0.01-4%), aloe vera extract (0.01-4%) imidazolidinyl urea (0.01-4%), propylparaben (0.01-4%), bha (0.01-4%), L-arginine hydrochloride (0.25% to 25%), sodium chloride (0.25% to 25%) magnesium chloride (0.25% to 25%).

An effective amount of a nitric oxide precursor is provided for increasing local blood flow in tissue The nitric oxide precursor is L-arginine, a salt, a complex or a derivative thereof. An effective amount of nitric oxide precursor is L-arginine glutamate (0.25-25%). L-arginine hydrochloride 0.25-25% provides a precursor to the molecule, nitric oxide, NO. Nitric oxide is the substance that relaxes the blood vessels, allowing for increased blood flow. This invention relates to topical application of a cream, gel, or other vehicle which contains substances such as L-arginine which delivers these substances into tissue for the purpose of producing beneficial effects based on improvement of local blood supply.

In another embodiment L-arginine further comprises a sufficient amount of ionic salt such as to create an ionic environment to cause absorption of the nitric oxide precursor. Choline chloride (0.25 to 25%), sodium chloride (0.25 to 25%) and magnesium chloride (0.25 to 25%) provides a high ionic strength environment for the highly charged molecule, L-arginine. This high ionic strength environment is an example of a hostile biophysical environment for L-arginine. That is, the highly charged ionic strength is an unfavorable environment for the highly charged L-arginine making the L-arginine anxious to move to a more hospitable, less charged environment such as human tissue. The base cream containing L-arginine (0.25 to 25%), choline chloride (0.25 to 25%), sodium chloride (0.25 to 25%) and magnesium chloride (0.25 to 25%) is the agent which produces beneficial effects such as hair growth, healing of ulcers such as leg ulcers or restoration of normal erectile function in males suffering from erectile dysfunction.

The cream in another embodiment, acts effectively to induce hair growth on human scalp lacking sufficient hair when applied nightly to the bald area each night for several months. Hair growth is naturally a slow process. However, substantial hair growth is achieved over large areas of scalp with results becoming evident in a few weeks and substantial within several months.

Yet further, the cream, in another embodiment, acts to promote healing of superficial ulcers such as those sometimes found on the legs of persons with severe diabetes. Application twice daily for a period of two weeks causes substantial healing and in many cases complete healing is achieved within this time period or slightly longer (3-4 weeks). This invention relates to topical application of a cream, gel, or other vehicle which contains substances such as L-arginine which delivers these substances into tissue for the purpose of producing beneficial effects through restoration of natural mechanisms based on improvement of local blood supply.

In another embodiment, the nitric oxide precursor may be administered with a trans-dermal patch, wherein the nitric oxide precursor is L-arginine, a salt, or a complex thereof. The trans-dermal patch in another embodiment, can further comprise a sufficient amount of ionic salts such as to create an ionic strength environment to cause tissue absorption of the L-arginine species.

Still further, in another embodiment, the cream acts to overcome erectile dysfunction in males causing restoration of natural sexual function. The method for overcoming impotence is by applying, through means of a delivery vehicle to the penis, an effective dose of a precursor to the endothelial relaxing factor, nitric oxide. The delivery vehicle is a penetrating cream, a liquid, a lotion, and ointment or other topical preparation containing L-arginine, salt or salts of L-arginine, a complex of L-arginine or a derivative of L-arginine in an effective dose. In another embodiment, a complex of L-arginine or a derivative of L-arginine in an effective dose is combined with ionic salts such as to create an ionic strength environment high enough to provide an extra force to cause tissue absorption of the L-arginine species.

These applications and others share as a common mechanism of action, improvement in local blood flow. A method for increasing local blood flow in tissue of a mammal is administering topically an effective amount of a nitric oxide precursor, wherein the nitric oxide precursor is either an L-arginine salt, complex or derivative thereof. An example providing an effective amount of nitric oxide precursor is by using L-arginine hydrochloride (0.25% to 25%) or L-arginine glutamate (0.25-25%). In the case of an alternative active agent were used it would be simply substituted for L-arginine in a delivery preparation. A sufficient amount of ionic salt such as to create an ionic environment may be included to cause absorption of the nitric oxide precursor.

Other Embodiments

Other Active Agents

While L-arginine hydrochloride (0.25 to 25%) is the preferred active agent because it is the agent in nature itself, it is non-toxic, is highly soluble and it is inexpensive, other agents could be used which are also precursors or donors of nitric oxide. These include D,L-arginine, L-arginine, alkyl (ethyl, methyl, propyl, isopropyl, butyl, isobutyl, t-butyl) esters of L-arginine and salts thereof. Pharmaceutically acceptable salts include hydrochloride, glutamate, butyrate, and glycolate.

In the case of an alternative active agent were used it would be simply substituted for L-arginine in a delivery preparation and the preparation used as in the case of the L-arginine preparation such as using either L-arginine hydrochloride (0.25 to 25%) or L-arginine glutamate (0.25 to 25%) instead of L-arginine.

Other Means of Effecting or Improving Absorption

A variety of means for effecting or improving absorption of the active agent can be envisioned, which are provided in the following several embodiments. One principle behind the absorption of a highly charged molecule such as L-arginine into tissue is to either create a biophysically hostile environment in the delivery vehicle such that L-arginine would prefer to be in tissue, or in an another embodiment is to package L-arginine in such a way that it is carried into tissue or neutralize its charge by derivitization or forming a neutral salt. Examples of biophysically hostile environments, include but are not limited to; high ionic strength by the addition of ionic salts such as sodium chloride, magnesium chloride or choline chloride; high or low pH by adding pharmaceutically acceptable acids or bases; and highly hydrophobic environments by decreasing water content and increasing lipid, oil and/or wax content.

Examples of the other embodiment of packaging which would be carried into tissue includes liposomes or emulsions of collagen, collagen peptides or other components of skin or basement membrane. Examples of neutralization of charge include delivery of the active agent in the form or an ester or salt such as arginine glutamate which is electronically neutral. In each case of creating a hostile biophysical environment for the active agent, the agent was added to an appropriate preparation.

In the case of creating a high ionic strength ions such as but not limited to sodium chloride, potassium chloride, choline chloride, magnesium chloride, lithium chloride, alone or in combination were added in high concentration. An example of a high concentration of high strength ions are sodium chloride (0.25% to 25%), choline chloride (0.25% to 25%) and magnesium chloride (0.25% to 25%) alone or. in combination.

Other highly charged molecules such as polylysine, polyglutamine, polyaspartate or copolymers of such charged amino acids may be used to create the hostile biophysical environment. Alternatively a hostile biophysical environment may be created by placing the highly charged L-arginine in an hydrophobic, oily environment such as in an oil-based cream containing little or no water.

Absorption may further be aided in another embodiment, by combining the use of hostile biophysical environments with the use of penetrating agents such as oleoresin capsicum or its constituents or molecules containing heterocyclic rings to which are attached hydrocarbon chains.

Example 1

In this example a 53 year old man with a scalp lacking sufficient hair consisting of a severely receding hairline as well as large "bald spot" on the top rear of his head was provided with a penetrating cream containing L-arginine hydrochloride (12.5% w/v), choline chloride (10% w/v), sodium chloride (5% w/v) and magnesium chloride (5% w/v). The cream was applied to the bald areas each night before going to bed and was rubbed in extensively for maximal absorption. New hair growth was noted within 2-3 weeks. Within 4 months the receding hairline (previously 4 cm of bald skin) had returned to normal and the "bald spot" previously more than 7 cm in diameter had been reduced to an area of less than 2 cm with even this area showing some new hair growth.

The method for promoting hair growth is to provide an effective dose of a nitric oxide precursor in a delivery vehicle wherein the delivery vehicle is a penetrating cream, a liquid, a lotion, an ointment or other topical preparation. The cream can comprise water (20-80%). mineral oil (3-18%)/glyceryl stearate SE (0.5-12%), squalene (0 2-12%), cetyl alcohol (0.1-11%), propylene glycol stearate SE (0.1-11%), wheat germ oil (0.1-6%), glyceryl stereate (0.1-6%), isopropyl myristate (0.1-6%), stearyl stearate (0.1-6%), polysorbate 60 (0.1-5%), propylene glycol (0.05-5%), tocopherol acetate (0.05-5%), collagen (0.05-5%), sorbitan stearate (0.05-5%), vitamin A&D (0.02-4%) triethanolamine (0 01-4%) methylparaben (0.01-4%), aloe vera extract (0.01-4%), imidazolidinyl urea (0.01-4%), propylparaben (0.01-4%), bha (0.01-4%), L-arginine hydrocholide (0.25% to 25%) sodium chloride (0.25% to 25%) magnesium chloride (0.25-25%) and choline chloride (0.25-25%).

Example 2

In a 54 year old man with a history of impotence twice daily administration of a penetrating cream containing L-arginine hydrochloride (12.5% w/v), choline chloride (10% w/v), sodium chloride (10% w/v) and magnesium chloride (5% w/v) directly to the penis twice daily for 7 days brought initial relief from the symptoms of impotence and allowed the subject to resume normal sexual activity. This relief of symptoms was maintained by continuation of the treatment daily.

A method to overcome impotence is by applying, through means of a delivery vehicle to the penis, an effective dose of a precursor to the endothelial relaxing factor, nitric oxide. The delivery vehicle is a penetrating cream, a liquid, a lotion, an ointment or other topical preparation containing L-arginine salt or salts of L-arginine, a complex of L-arginine or a derivative of L-arginine in an effective dose.

In another embodiment, the delivery vehicle in addition to the effective dose of L-arginine may contain ionic salts such as to create an ionic strength environment high enough to provide an extra force to cause tissue absorption of the L-arginine species.

In another embodiment, the method for overcoming impotence has the delivery vehicle in the form of a cream that can comprise water (20-80%), mineral oil (3-18%), glyceryl stearate (0.25%-12%), squalene (0.2-12%), wheat germ oil (0.1-6%), cetyl alcohol (0 1-11%), propylene glycol stearate SE (0.1-11%), polysorbate 60 (0.1-5%), propylene glycol (0.05-5%), vitamin E (0.02-4%) hyaluronic acid/collagen (0.05-5%), vitamin A& D (0.02-4%), sorbitan stearate (0.05-5%) triethanolamine (0.01-4%), imidazolidinyl urea (0.01-4%), methylparaben (0.01-4%), propylparaben (0.01-4%), bha 0.01-4%), aloe vera extract 0.01-4%), L-arginine hydrochloride (0.25% to 25%) and sodium chloride (0.25% to 25%) choline chloride (0.25-25%) and magnesium chloride (0.25-25%).

Example 3

In a 62 year old man with a history of impotence placed a condom containing a water based penetrating cream containing L-arginine hydrochloride (12.5% w/v), choline chloride (10% w/v), sodium chloride (5% w/v) and magnesium chloride (5% w/v) was warn on the flaccid penis for 30-60 minutes before erection was desired. At that time, when sexual performance was needed, an erection was easily obtained and normal sexual activity was conducted.

Accordingly, it can be seen that in the present invention I have provided nitric oxide precursor agents, L-arginine and its derivatives, which when applied to scalp lacking sufficient hair causes hair growth through utilization of one of the body's own mechanisms. This effect is achieved by providing the biochemical substrate at the local site from which nitric oxide is produced. Nitric oxide causes increased local blood flow, which enables the growth of hair.

Further I have provided nitric oxide precursor agents, L-arginine and its derivatives, which when applied to leg ulcers cause healing through use of the body's own mechanisms. This effect is achieved by providing the biochemical substrate at the local site from which the controlling substance, nitric oxide is produced. Nitric oxide causes increases in local blood flow allowing the body's own healing cells and substances to reach the ulcer site. A method for increasing local blood flow in tissue is administering topically an effective amount of a nitric oxide precursor, wherein the nitric oxide precursor is either an L-arginine salt complex or derivative thereof. An effective amount of nitric oxide precursor is L-arginine hydrochloride (0.25% to 25%) or L-arginine glutamate (0.25-25%).

Still further I have provided nitric oxide precursor agents, L-arginine and its derivatives, that when applied to a penis subject to erectile dysfunction causes restoration of normal sexual function.

Although the description above contains many specificities, these should not be construed as limiting in this scope of the invention but as merely providing illustrations of some of the presently preferred embodiments of this invention. Various other embodiments and ramifications are possible within the scope. Thus the scope of the invention should be determined by the appended claims and their legal equivalents, rather than by the examples given.

What is claimed is:

1. A method of increasing localized bloodflow in tissue by delivering to skin an L-arginine derivative, the method comprising the step of:

applying topically to the skin a delivery vehicle for the L-arginine derivative, said delivery vehicle comprising an amount of the L-arginine derivative effective to increase localized tissue bloodflow when combined with an agent for creating a hostile biophysical environment comprising an ionic salt mixture comprising choline chloride, sodium chloride, and magnesium chloride, the agent being at a concentration sufficient to create the hostile biophysical environment, the hostile biophysical environment causing the L-arginine derivative to migrate from the delivery vehicle to the skin where the L-arginine derivative is absorbed by tissue in the area surrounding the skin where the L-arginine derivative is applied.

2. The method of claim 1 wherein the delivery vehicle is selected from the group consisting of topical creams, topical liquids, topical lotions, and topical ointments, wherein the ionic salt mixture comprises, by weight, sodium chloride (0.25% to 25%), choline chloride (0.25% to 25%), and magnesium chloride (0.25% to 25%).

3. The method of claim 1 wherein the delivery vehicle is a hydrophobic delivery vehicle comprising the L-arginine derivative and the ionic salt mixture, the ionic salt mixture comprising, by weight, sodium chloride (0.25% to 25%), choline chloride (0.25% to 25%), and magnesium chloride (0.25% to 25%).

4. The method of claim 1 wherein the act of applying comprises applying a transdermal patch comprising the L-arginine derivative and a penetrating agent to the skin.

5. A method of delivering to skin a nitric oxide releasing substance selected from the group consisting of L-arginine, L-arginine salts, and L-arginine derivatives, the method comprising the step of:

applying topically to the skin a delivery vehicle for the substance, said delivery vehicle comprising the substance and an ionic salt at a concentration sufficient to create a hostile biophysical environment, the hostile biophysical environment causing the substance to migrate from the delivery vehicle to the skin where the substance is absorbed by tissue, wherein said delivery vehicle comprises, by weight, water (20%-80%), mineral oil (3%-18%), glyceryl stearate (0.5%-12%), squalene (0.2%-12%), cetyl alcohol (0.1%-11%), propylene glycol stearate (0.1%-11%), wheat germ oil (0.1%-6%), glyceryl stereate (0.1%-6%), isopropyl myristate (0.1%-6%), stearyl stereate (0.1%-6%), polysorbate 60 (0.1%-5%), propylene glycol (0.05%-5%), tocopherol acetate (0.05%-5%), collagen (0.05%-5%), sorbitan stearate (0.05%-5%), vitamin A&D (0.02%-4%), triethanolamine (0.01%-4%), methylparaben (0.01%-4%), aloe vera extract (0.01%-4%), imidazolidinyl urea (0.01%-4%), propylparaben (0.01%-4%), bha (0.01%-4%), L-arginine hydrocholide (0.25% to 25%), sodium chloride (0.25% to 25%), and magnesium chloride (0.25% to 25%).

6. The method of claim 5 wherein the delivery vehicle further comprises choline chloride (0.25%-25% by weight).

7. The method of claim 5 wherein the delivery vehicle further comprises L-arginine glutamate (0.25%-25% by weight).

8. A method of treating impotence in a male comprising:

delivering to a penis a substance that is a nitric oxide precursor selected from the group consisting of L-arginine and L-arginine derivatives by topically applying to the penis a delivery vehicle for the substance, said delivery vehicle comprising an amount of the substance effective to increase bloodflow in the penis when combined with an agent for creating a hostile biophysical environment at a concentration sufficient to create the hostile biophysical environment, the hostile biophysical environment causing the substance to migrate from the delivery vehicle to the penis where the substance is absorbed by the penis.

9. The method of claim 8 wherein the delivery vehicle is selected from the group consisting of topical creams, topical liquids, topical lotions, and topical ointments, the substance is L-arginine hydrochloride, 0.25% to 25% by weight, the delivery vehicle further comprising an ionic salt mixture comprising choline chloride at 10% by weight, sodium chloride at 10% by weight, and magnesium chloride at 5% by weight.

10. The method of claim 8 wherein the delivery vehicle is a hydrophobic delivery vehicle comprising the substance, wherein the substance is L-arginine hydrochloride at 12.5% by weight, and wherein the delivery vehicle further comprises an ionic salt mixture comprising choline chloride at 10% by weight, sodium chloride at 10% by weight and magnesium chloride at 5% by weight.

11. A method of treating impotence in a male by delivering to skin a nitric oxide releasing substance selected from the group consisting of L-arginine, L-arginine salts, and L-arginine derivatives, the method comprising the step of:

applying topically to a penis a delivery vehicle for the substance, said delivery vehicle comprising the substance and an ionic salt at a concentration sufficient to create a hostile biophysical environment, the hostile biophysical environment causing the substance to migrate from the vehicle to the penis where the substance is absorbed by tissue, wherein said delivery vehicle comprises, by weight, water (20%-80%), mineral oil (3%-18%), glyceryl stearate (0.5%-12%), squalene (0.2%-12%), cetyl alcohol (0.1%-11%), propylene glycol stearate (0.1%-11%), wheat germ oil (0.1%-6%), glyceryl stereate (0.1%-6%), isopropyl myristate (0.1%-6%), stearyl stereate (0.1%-6%), polysorbate 60 (0.1%-5%), propylene glycol (0.05%-5%), tocopherol acetate (0.05%-5%), collagen (0.05%-5%), sorbitan stearate (0.05%-5%), vitamin A&D (0.02%-4%), triethanolamine (0.01%-4%), methylparaben (0.01%-4%), aloe vera extract (0.01%-4%), imidazolidinyl urea (0.01%-4%), propylparaben (0.01%-4%), bha (0.01%-4%), L-arginine hydrocholide (0.25% to 25%), sodium chloride (0.25% to 25%), and magnesium chloride (0.25% to 25%).

12. The method of claim 11 wherein the delivery vehicle further comprises choline chloride (0.25%-25% by weight).

13. The method of claim 11 wherein the delivery vehicle further comprises L-arginine glutamate (0.25%-25% by weight).

14. The method according to any one of claims 8-10 and 11-13 wherein the delivery vehicle is contained in a condom which is placed on the penis.

15. A method of promoting hair growth by delivering, to a selected area of skin where hair growth is desired, a nitric oxide releasing substance selected from the group consisting of L-arginine, L-arginine salts, and L-arginine derivatives, the method comprising:

topically applying, to the selected area of the skin where hair growth is desired, a delivery vehicle for the substance, said delivery vehicle comprising the substance and an ionic salt at a concentration sufficient to create a hostile biophysical environment, the hostile biophysical environment causing the substance to migrate from the delivery vehicle to the selected area of the skin where hair growth is desired, where the substance is absorbed by the selected area of the skin, wherein said delivery vehicle comprises, by weight water (20%-80%), mineral oil (3%-18%), glyceryl stearate (0.5%-12%), squalene (0.2%-12%), cetyl alcohol (0.1%-11%), propylene glycol stearate (0.1%-11%), wheat germ oil (0.1%-6%), glyceryl stereate (0.1%-6%), isopropyl myristate (0.1%-6%), stearyl stereate (0.1%-6%), polysorbate 60 (0.1%-5%), propylene glycol (0.05%-5%), tocopherol acetate (0.05%-5%), collagen (0.05%-5%), sorbitan stearate (0.05%-5%), vitamin A&D (0.02%-4%), triethanolamine (0.01%-5%), methylparaben (0.01%-4%), aloe vera extract (0.01%-4%), imidazolidinyl urea (0.01%-4%), propylparaben (0.01%-4%), bha (0.01%-4%), L-arginine hydrocholide (0.25% to 25%), sodium chloride (0.25% to 25%), and magnesium chloride (0.25% to 25%).

16. The method of claim 15 wherein the delivery vehicle further comprises choline chloride (0.25%-25% by weight).

17. The method of claim 15 wherein the delivery vehicle further comprises L-arginine glutamate (0.25%-25% by weight).

18. A method of delivering to skin an L-arginine derivative, the method comprising the step of:
topically applying to the skin a delivery vehicle for the L-arginine derivative, said delivery vehicle comprising the L-arginine derivative at a concentration of 0.25% to 25% by weight, the L-arginine derivative contained within packaging selected from the group consisting of a liposome, an emulsion of collagen, and a collagen peptide, said packaging being at a concentration within the delivery vehicle sufficient to create an hostile biophysical environment, the hostile biophysical environment causing the packaging to migrate from the delivery vehicle to the skin where the L-arginine derivative is released from the packaging and absorbed by tissue, wherein the delivery vehicle is applied to the penis.

19. A method of delivering to skin an L-arginine derivative, the method comprising the step of:
topically applying to the skin a delivery vehicle for the L-arginine derivative, said delivery vehicle comprising the L-arginine derivative at a concentration of 0.25% to 25% by weight, the L-arginine derivative contained within packaging selected from the group consisting of a liposome, an emulsion of collagen, and a collagen peptide, said packaging being at a concentration within the delivery vehicle sufficient to create an hostile biophysical environment, the hostile biophysical environment causing the packaging to migrate from the delivery vehicle to the skin where the L-arginine derivative is released from the packaging and absorbed by tissue, wherein the delivery vehicle is applied to a selected area of skin where hair growth is desired.

20. The method of increasing localized bloodflow in tissue of claim 1 wherein the effective amount of the substance is 0.25% to 25% by weight of the delivery vehicle.

21. The method of increasing localized bloodflow in tissue of claim 1, wherein the agent for creating a hostile biophysical environment has a concentration of 0.25% to 25% by volume of the delivery vehicle.

22. The method of increasing localized bloodflow in tissue of claim 1, wherein the delivery vehicle further comprises an agent selected from the group consisting of a pharmaceutically acceptable acid, a pharmaceutically acceptable base, polylysine, polyglutamine, polyasparate, and copolymers of charged amino acids.

23. The method of treating impotence of claim 8 wherein the effective amount of the substance is 0.25% to 25% by weight of the delivery vehicle.

24. The method of treating impotence of claim 8 wherein the agent for creating a hostile biophysical environment is a salt selected from the group consisting of sodium chloride, choline chloride, potassium chloride, lithium chloride, magnesium chloride, and mixtures thereof.

25. The method of treating impotence of claim 24 wherein the agent for creating a hostile biophysical environment has a concentration of 0.25% to 25% by volume of the delivery vehicle.

26. The method of treating impotence of claim 8 wherein the agent for creating a hostile biophysical environment is selected from the group consisting of a pharmaceutically acceptable acid, a pharmaceutically acceptable base, polylysine, polyglutamine, polyasparate, and copolymers of charged amino acids.

* * * * *